US008406845B2

(12) United States Patent
Komistek et al.

(10) Patent No.: US 8,406,845 B2
(45) Date of Patent: Mar. 26, 2013

(54) METHOD AND APPARATUS FOR IMAGING TRACKING

(75) Inventors: Richard D. Komistek, Knoxville, TN (US); William R. Hamel, Farragut, TN (US); Douglas A. Dennis, Littleton, CO (US)

(73) Assignee: University of Tennessee Research Foundation, Knoxville, TN (US)

( * ) Notice: Subject to any disclaimer, the term of this patent is extended or adjusted under 35 U.S.C. 154(b) by 2055 days.

(21) Appl. No.: 11/217,198

(22) Filed: Sep. 1, 2005

(65) Prior Publication Data

US 2006/0058645 A1  Mar. 16, 2006

Related U.S. Application Data

(60) Provisional application No. 60/606,480, filed on Sep. 1, 2004, provisional application No. 60/607,658, filed on Sep. 7, 2004.

(51) Int. Cl.
*A61B 5/05* (2006.01)
(52) U.S. Cl. ........ 600/407; 600/410; 600/425; 600/429; 378/20; 378/195
(58) Field of Classification Search .......... 378/195–198; 600/407, 425, 429
See application file for complete search history.

(56) References Cited

U.S. PATENT DOCUMENTS

| | | | | |
|---|---|---|---|---|
| 4,501,011 A * | 2/1985 | Hauck et al. | ............... | 378/196 |
| 5,255,680 A * | 10/1993 | Darrow et al. | ............... | 600/424 |
| 5,727,554 A * | 3/1998 | Kalend et al. | ............... | 600/587 |
| 5,873,822 A * | 2/1999 | Ferre et al. | ............... | 600/407 |
| 6,155,713 A * | 12/2000 | Watanabe | ............... | 378/197 |
| 6,254,553 B1 * | 7/2001 | Lidgren et al. | ............... | 601/3 |
| 6,413,216 B1 * | 7/2002 | Cain et al. | ............... | 600/439 |
| 6,889,695 B2 * | 5/2005 | Pankratov et al. | ............... | 128/898 |
| 6,996,431 B2 * | 2/2006 | Ben-Haim et al. | ............... | 600/407 |
| 7,096,055 B1 * | 8/2006 | Schweikard | ............... | 600/407 |
| 7,331,712 B2 * | 2/2008 | Fischer et al. | ............... | 378/203 |
| 7,544,172 B2 * | 6/2009 | Santos-Munne et al. | ......... | 601/5 |
| 7,567,834 B2 * | 7/2009 | Clayton et al. | ............... | 600/424 |
| 7,860,550 B2 * | 12/2010 | Saracen et al. | ............... | 600/410 |
| 2002/0087062 A1 * | 7/2002 | Schmidt et al. | ............... | 600/407 |
| 2002/0091314 A1 * | 7/2002 | Schlossbauer et al. | ....... | 600/407 |
| 2002/0123681 A1 * | 9/2002 | Zuk et al. | ............... | 600/410 |
| 2002/0193685 A1 * | 12/2002 | Mate et al. | ............... | 600/424 |
| 2003/0091155 A1 * | 5/2003 | Crain et al. | ............... | 378/197 |
| 2003/0091156 A1 * | 5/2003 | Crain et al. | ............... | 378/197 |
| 2004/0024309 A1 * | 2/2004 | Ferre et al. | ............... | 600/424 |
| 2004/0215075 A1 * | 10/2004 | Zagzebski et al. | ............... | 600/442 |
| 2005/0049486 A1 * | 3/2005 | Urquhart et al. | ............... | 600/429 |

(Continued)

OTHER PUBLICATIONS

Hoover, Aaron, For Orthopedic Injuries, A Robot That Follows Patients As They Move, University of Florida News, Jan. 19, 2006, Gainsville, Florida.

(Continued)

*Primary Examiner* — Brian Casler
*Assistant Examiner* — Nasir S Shahrestani
(74) *Attorney, Agent, or Firm* — Taft Stettinius & Hollister LLP

(57) ABSTRACT

Image tracking systems, and corresponding methods, are described. In some embodiments, conventional imaging components are placed on a platform having wheels, thereby providing a mechanism for imaging a moving subject. In other embodiments, conventional imaging components are situated on non-parallel rails, and moved along those rails, thereby providing a mechanism for imaging an anatomical region of a subject as that region moves in two dimensions. For yet other embodiments, image recognition and tracking approaches are provided to track the movement of a non-stationary anatomical region. The tracking of the non-stationary anatomical region permits imaging of a moving anatomy. For some embodiments, the anatomy moves within its normal range of motion.

26 Claims, 12 Drawing Sheets

U.S. PATENT DOCUMENTS

| | | | |
|---|---|---|---|
| 2005/0119565 A1* | 6/2005 | Pescatore | 600/429 |
| 2005/0234327 A1* | 10/2005 | Saracen et al. | 600/407 |
| 2006/0025677 A1* | 2/2006 | Verard et al. | 600/423 |
| 2006/0029181 A1* | 2/2006 | Chen et al. | 378/17 |
| 2006/0100509 A1* | 5/2006 | Wright et al. | 600/426 |
| 2006/0142657 A1* | 6/2006 | Quaid et al. | 600/424 |
| 2006/0241369 A1* | 10/2006 | Lienard et al. | 600/407 |
| 2007/0015991 A1* | 1/2007 | Fu et al. | 600/407 |
| 2009/0275867 A1* | 11/2009 | Santos-Munne et al. | 601/5 |
| 2010/0317968 A1* | 12/2010 | Wright et al. | 600/427 |

OTHER PUBLICATIONS

Hamel, et al., Update on the Prototype Tracking Fluoroscope System, Center for Musculoskeletal Research, [date unknown but prior to Sep. 1, 2005], Univ. of Tenn., Knoxville, Tenn.

* cited by examiner

METHOD AND APPARATUS FOR IMAGING TRACKING

CROSS REFERENCE TO RELATED APPLICATIONS

This application claims priority to and the benefit of provisional patent applications, Ser. No. 60/606,480 filed Sep. 1, 2004 and Ser. No. 60/607,658 filed Sep. 7, 2004.

FIELD OF THE INVENTION

The present disclosure relates generally to imaging and, more particularly, to medical imaging.

BACKGROUND

Many medical imaging modalities currently exist. These imaging modalities include x-ray fluoroscopy, magnetic resonance imaging (MRI), ultrasound, and a host of others that are known in the art. Each of these imaging modalities has its own unique advantages and disadvantages. For example, MRI utilizes a relatively benign radio-frequency (RF), as compared to x-ray imaging which emits ionizing radiation. However, when compared to x-ray imaging equipment, MRI equipment is quite costly. Hence, the cost of obtaining an MRI is greater than the cost of obtaining an x-ray.

In conventional fluoroscopy, which is well known in the art, ionizing radiation passes through the body onto a fluorescent screen, creating an image. Fluoroscopy is often used to trace contrast media as it passes through the body. Often, moving x-ray images from fluoroscopy can be captured to film or video, thereby allowing for time-resolution of the fluoroscopic images. Conventional fluoroscopy is routinely used to analyze the human skeletal joints during motions such as deep knee bends. Such diagnostics have been used to characterize pre and post operative arthoplasty issues, particularly in association with total joint replacement procedures. The pseudo-stationary conditions imposed by the fixed fluoroscope limit the diagnostic procedures to much less than natural skeletal motion and load conditions, thus reducing the utility of the results.

While such imaging modalities have become powerful diagnostic tools, there are still many limitations associated with these imaging modalities. For example, conventional fluoroscopy does not allow selected joints to be x-rayed while the human subjects perform natural motions, such as walking, under loaded conditions. This disclosure seeks to address some of those limitations.

SUMMARY

The image tracking system of the present disclosure provides a system and method to mechanize the process of orthopedic diagnostics such that diagnostics of a subject can be accomplished while the subject performs natural motions under loaded conditions. The image tracking system provides a subject imaging system that dynamically positions the imaging system line of sight during natural motions providing orthopedists and researchers with in vivo information not previously available. In particular, the image tracking system of the present disclosure provides dynamic imaging of an anatomical region of interest of a subject, such as a selected anatomical section, such as a skeletal section. For example, the system is capable of dynamic imaging of a selected joint, such as an ankle, knee, hip, elbow or shoulder joint. The system can also provide imaging of a selected skeletal section, such as a portion of the cervical spine, providing dynamically imaged large torso movement. The image tracking system of the present disclosure provides active control functions for tracking movement of a specific anatomical section, and optionally subject tracking, for imaging the section.

As a subject walks, for example, the leg joints move vertically and horizontally with respect to the subject's body. The fastest of these motions is associated with ankles. To accommodate specific joint tracking, the drive mechanisms for the imaging system are located on each side of the imaging cavity of the image tracking system. These drives provide mechanisation necessary to assure the imaging system's line of sight is synchronized from side to side and that it tracks the movement of the joint or skeletal section of interest. In an exemplary embodiment, the joint of skeletal section tracking is accomplished by using image frames from the imaging system and image processing to ascertain where the joint or bone features of interest are located relative to the image detector/intensifier in real time. The drive mechanisms for the image source and separate image detector operate the positioning of the detector and source to keep the joint/skeletal bone image of interest in the center of the filed of view of the image.

Optional subject tracking is provided by a frame and wheel drive system for the imaging tracking system. Separate steerable independent drive motors and drive wheels provide omni-directional translation capability. Motion motors for the drive wheels are speed controlled and steering motors for the drive wheels are positioned controlled. Thus, as the subject walks about a room, the image tracking system can follow along with the subject keeping the subject centered within the imaging cavity of the system. An exemplary technique for subject tracking includes computer vision for determining the subject's position and orientation with respect to the imaging cavity of the system. Three translation modes are accommodated by the system, namely 1) front to back translation, such as for imaging ankles and knees, 2) side to side translation, such as for imaging hips, and 3) translation in an arbitrary direction allowing the subject to simply walk about a room with the image tracking system "tagging along". All together, the image tracking system includes at least eight degrees of freedom that are used to accomplish joint and subject tracking.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figure 1:
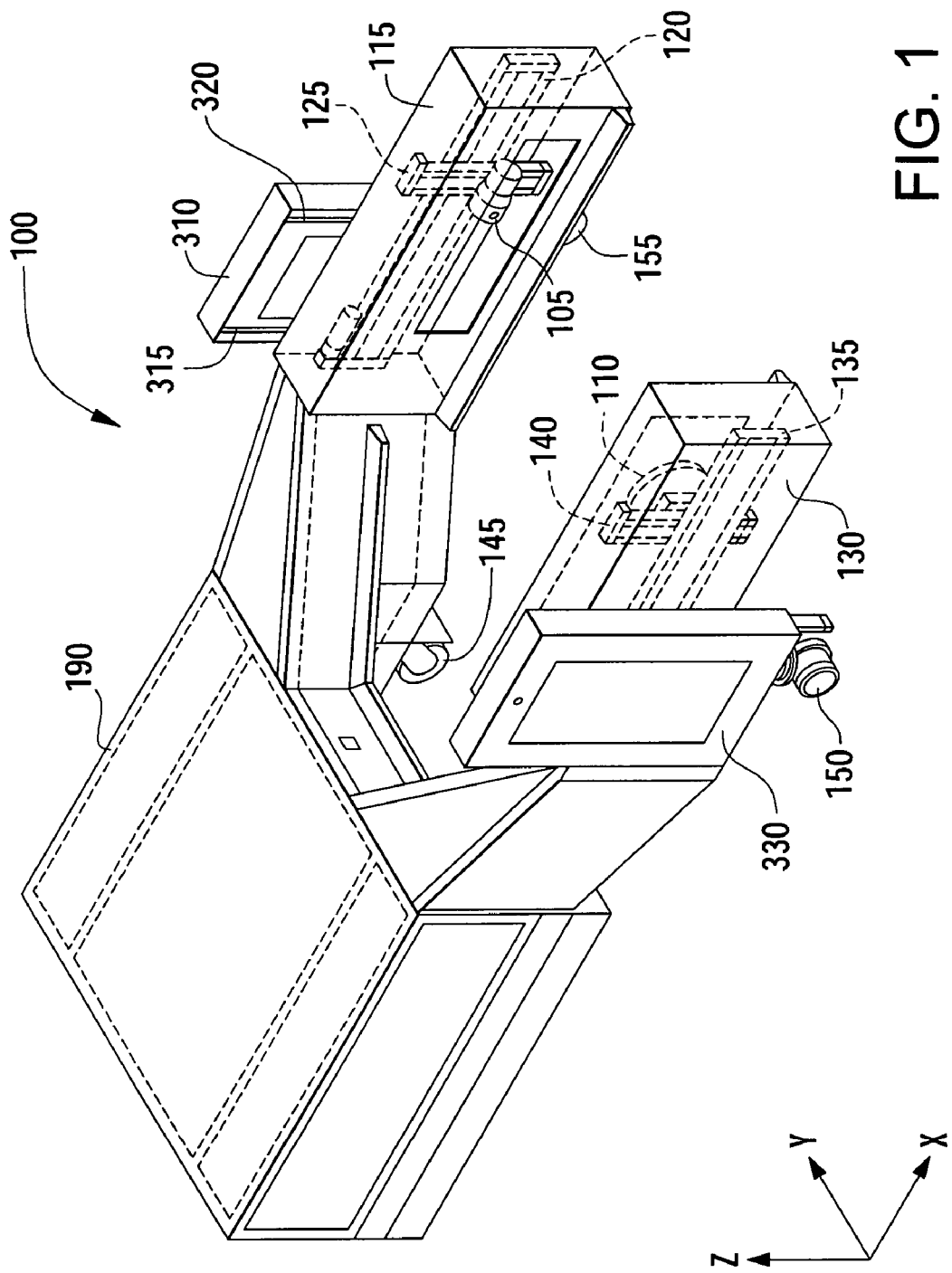
FIG. 1 is a right perspective view of an exemplary embodiment of an image tracking system of the present invention.

While various embodiments are disclosed in the following drawings and detailed description, other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims.

DETAILED DESCRIPTION OF THE EMBODIMENTS

Reference is now made in detail to the description of the embodiments as illustrated in the drawings. While several embodiments are described in connection with these drawings, there is no intent to limit the invention to the embodiment or embodiments disclosed herein. On the contrary, the intent is to cover all alternatives, modifications, and equivalents.

Typically, imaging systems are stationary objects, which have predefined footprints and are relatively immobile during examination of a patient or subject. For example, conventional fluoroscopes and magnetic resonance imaging (MRI) systems are installed in one location, and typically occupy that location until they are removed or reinstalled to another location.

Fluoroscopic methods have been developed in which human skeletal joints are analyzed during motions, such as, for example, deep knee bends. Such methods are used to characterize pre-operative and post-operative issues, particularly in association with total joint replacement procedures. The pseudo-stationary conditions imposed by the fixed fluoroscope limit the diagnostic procedures to much less than natural skeletal motion and load conditions, thereby reducing the utility of the results obtained from such pseudo-stationary conditions. Unfortunately, there is no convenient approach to acquiring those images as the joints under normal conditions of stresses and strains.

Several embodiments of systems and methods are presented below, in which components of a conventional imaging system are mounted onto a moving frame. The moving frame permits imaging of various anatomical features (e.g., ankles, knees, hips, shoulders, spine, etc.), as those features move within their normal range of motion (e.g., walking, running, etc.). This may be sometimes referred to herein as feature tracking or joint/skeletal tracking. In some embodiments, the entire unit is configured to move, thereby providing an imaging system that can track a subject's movements, sometimes referred to as subject tracking. In other embodiments, the components of the imaging system are mounted onto rails, thereby permitting travel of the imaging-system components in various directions. For example, by mounting components of a fluoroscope on two orthogonal tracks (e.g., along an x-axis and a z-axis), it is possible to move those components along both axes. This movement permits tracking and imaging of anatomical features that may be moving along these two directions.

For yet other embodiments, the two-dimensional (2D) motion can be combined with the mobile platform, thereby permitting three-dimensional (3D) tracking of moving anatomical features.

For example, images of a naturally flexing human knee, such as during walking or running, can be tracked and acquired using such a system. Briefly, the system is configured to track the time-varying location of the knee as the subject walks or runs, and dynamically move the imaging components to match the time-varying location of the knee. By dynamically tracking and adjusting the imaging components, the knee can be imaged as it moves within its natural range of motion.

Various embodiments, which describe specific systems and methods for dynamic tracking and imaging of anatomical features, are provided below with reference to FIGS. 1 through 9.

FIG. 1 is a right perspective view of an exemplary embodiment of an image tracking system 100. As shown in FIG. 1, the image tracking system 100, for this embodiment, is equipped with an imaging system consisting of a radiation source 105 (also abbreviated as "source") and a radiation detector 110 (also abbreviated as "detector"). As is known in the art, the detector 110 can include an image intensifier or other known imaging components that facilitate detection of the emitted radiation. The source 105 and the detector 110, in combination, permit fluoroscopy of a subject or patient when the subject or patient is positioned between the source 105 and the detector 110.

In an exemplary embodiment, the source 105 is an x-ray fluoroscopic source that is located on one side of the image tracking system 100, with the detector 110 located on the other side of the image tracking system 100. As the x-ray beam crosses from the source 105 to the detector 110, the beam passes through the subject's anatomical region of interest (ROI). Bones and hard tissue absorb more x-ray energy than soft tissues, thereby resulting in a 2D gray scale image of the skeletal features.

In some embodiments, a typical fluoroscopic source 105 and detector 110 are employed. These components provide a spatial resolution of approximately 800×400 pixels, a 16-bit gray scale, and a frame capture rate of approximately fifteen to thirty frames per second (fps). It should be appreciated that, for other embodiments, the spatial and temporal resolution can be increased or decreased to accommodate various imaging needs. Such modifications are discussed below in greater detail.

Metallic implants appear as very dark images, while high-density polyethylene bearings are nearly transparent. Commonly, image intensifiers (not shown) convert the x-rays into visible light, which can be captured by a digital camera system. Techniques have been developed to extract the features of the desired joint from the digital images, as discussed in greater detail below. For example, if knee joints are being studied, then both knees will appear in the field of view (FOV) and it would be desirable to isolate the features of the knee of interest. The extraction of the features of interest is discussed in greater detail below.

While exemplary embodiments are described with reference to x-ray fluoroscopy, it should be appreciated that the various embodiments can be readily modified to accommodate other imaging modalities. For example, while an x-ray source 105 and detector 110 are described herein, it should be appreciated that other source-detector combinations can be used for different imaging modalities.

The image tracking system 100 also includes a frame 190, which provides the underlying support for the components of the image tracking system 100. Since a subject will be placed between the source 105 and the detector 110, the frame 190 has an opening, or imaging cavity, that facilitates the placement of the subject between the source 105 and the detector 110. In the embodiment of FIG. 1, the imaging cavity is substantially in the shape of a tuning fork, with the source 105 being placed on one arm of the tuning-fork-like structure, and the detector being placed on the other arm of the tuning-fork-like structure. In that regard, when a subject or patient is placed within the imaging cavity between the arms of the tuning-fork-like structure, the source 105 and the detector 110, in combination, permit fluoroscopic imaging of the subject.

In some embodiments, among others, the frame exhibits substantial plane symmetry across the x-z plane. For simplicity, the front of the image tracking system 100 is described herein as being in the +x-direction, while the back of the image tracking system 100 is described as being in the −x-direction. Also, the top of the image tracking system 100 is described as being in the +z-direction, while the bottom of the image tracking system 100 is described as being in the −z-direction. Additionally, the left side and the right side of the image tracking system 100 is described as being in the +y-direction and −y-direction, respectively.

The frame 190 also provides the support structure for the mechanisms that are related to three-dimensional (3D) movement of the imaging components. Horizontal rails 120, 135 and vertical rails 125, 140 control movement in two of the three dimensions, namely, the x-direction and z-direction as shown in FIG. 1.

The source 105 is mounted onto both a horizontal source rail 120 and a vertical source rail 125. The horizontal source rail 120 provides movement of the source 105 in the x-direction, while the vertical source rail 125 provides movement of the source 105 in the z-direction. Similarly, the detector 110 is mounted onto both a horizontal detector rail 135 and a vertical detector rail 140. Similar to the source rails 120, 125, the detector rails 135, 140 permit movement of the detector 110 in the x-direction and the z-direction. It should be appreciated that, in a preferred embodiment, the source 105 and the detector 110 are configured to move synchronously, thereby permitting alignment of the detector 110 to the source 105 as the source 105 moves. The motorized driving mechanisms that are responsible for moving the source 105 and the detector 110 in the x-direction and z-direction are provided in greater detail below.

The source 105 and its corresponding rails 120, 125 are surrounded by a shielded source housing 115 (also abbreviated as "source housing"). In a preferred embodiment, the source 105 is configured to travel in both the x-direction and the z-direction within the source housing 115. In that regard, the source housing 115 includes an opening, through which the source 105 can emit radiation. Since the dosage and parameters of conventional fluoroscopic radiation sources is known in the art, no further discussion of fluoroscopic sources is discussed with reference to FIG. 1.

The detector 110 and its corresponding rails 135, 140 are surrounded by a shielded detector housing 130 (also abbreviated as "detector housing"). In a preferred embodiment, the detector 110 is configured to travel in both the x-direction and the z-direction within the detector housing 130, similar to how the source 105 travels within the source housing 115. In that regard, the detector housing 130 also includes an opening, similar to the opening in the source housing 115, through which the detector 110 can detect radiation that is emitted from the source 105.

The source housing 115 is mounted onto one of the tuning-fork-like arms, in the embodiment of FIG. 1. Specifically, the tuning-fork-like arm, on which the source housing 115 is mounted, comprises a left bracket 310 with two housing rails, designated in FIG. 1 as a left posterior housing rail 315 and a left anterior housing rail 320. Similarly, the tuning-fork-like arm, on which the detector housing 130 is mounted, comprises a right bracket 330 with two housing rails, designated as a right posterior housing rail 350 and a right anterior housing rail 355. These housing rails 315, 320, 350, 355 permit coarse adjustment of the height of both the source 105 and the detector 110 in the z-direction. The rails 120, 125, 135, 140 within the housings 115, 130 permit fine adjustment of the source 105 and the detector 110 in both the x-direction and the z-direction. The height adjustment mechanisms are discussed in greater detail below.

Movement of the imaging components in the third dimension, namely, the y-direction as shown in FIG. 1, is controlled in part by mechanisms that are related to the mobility of the image tracking system 100. In addition to providing support for the imaging components, such as the source 105 and the detector 110, the frame 190 provides support for the mobility-related mechanisms of the image tracking system 100. These mechanisms include, for example, a motorized front wheel 150, a passive front wheel 155, a passive left center wheel 145, and a host of other mechanisms, which are described in greater detail below.

While the disclosed embodiments include wheels that provide mobility to the system, it should be appreciated that the wheels are optional. In that regard, a subject can be placed on a treadmill, thereby substantially fixing the relative motion between the subject and the image tracking system 100. For those embodiments, as the subject walks on the treadmill, the source 105 and the detector 110 track the movements of the anatomical region of interest, while the image tracking system 100, as a whole, remains relatively stationary.

The operation of the image tracking system 100 is discussed in greater detail with reference to FIG. 2, which shows a right perspective view of the image tracking system 100, with a subject 200 that is positioned for imaging within the image tracking system 100. Additionally, FIG. 2 shows various internal components of the image tracking system 100, which are responsible for carrying out the various functions of the image tracking system 100.

Figure 2:
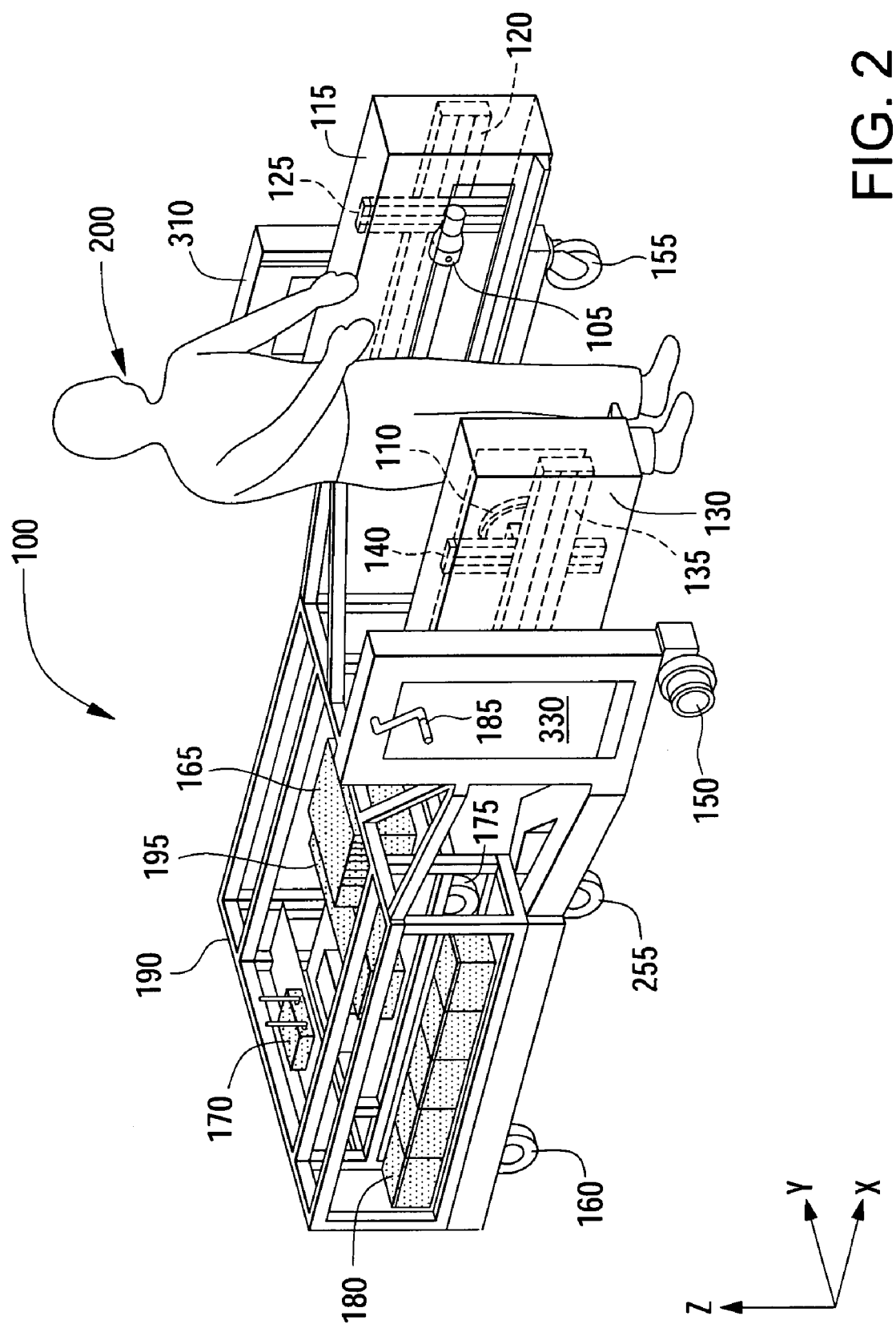
FIG. 2 is a right perspective view showing a subject positioned for imaging by the image tracking system of FIG. 1.

As shown in FIG. 2, a subject 200 is positioned between the left bracket 310 and the right bracket 330. In that regard, depending on the position of the source 105 and the detector 110, a portion of the subject's anatomy is placed within the imaging field that is created between the source 105 and the detector 110. The source 105 and detector 110 are coarsely aligned to a specific anatomy of interest (e.g., ankles, knees, hips, etc.) using a coarse height-adjustment mechanism 185. In some embodiments, the coarse height-adjustment mechanism 185 can be a handle that is coupled to a set of gears and/or cogs (not shown), which are in turn coupled to the housings 115, 130. In that regard, when an operator turns the handle, the height (y-direction) of the housings 115, 130 is coarsely adjusted through the corresponding turns of the gears/cogs. Since such mechanical height-adjusting mechanisms are known in the art, and since one having ordinary skill in the art can readily build such mechanisms, given the above-described operation, no further discussion of the coarse height-adjusting mechanism is provided herein.

In FIG. 2, the source 105 and the detector 110 are positioned by the coarse height-adjusting mechanism 185 at approximately knee-height on the subject 200. Also, in FIG. 2, the subject 200 is positioned so that the superior-inferior axis of the subject 200 is aligned in the z-direction, the lateral axis of the subject 200 is aligned in the y-direction, and the anterior-posterior axis of the subject 200 is aligned in the x-direction. Thus, when the subject 200 moves forward, from the subject's frame of reference, that direction will be along the x-axis in FIG. 2.

Also shown in FIG. 2 are a passive right center wheel 255, which is substantially symmetrically disposed across the x-z plane from the passive left center wheel 145. Both the passive right center wheel 255 and the passive left center wheel 145 are mechanically coupled to the frame 190 through casters, which permit relatively easy pivoting of the wheels as the image tracking system 100 travels within the x-y plane. Shown more clearly in FIG. 2 is the motorized front wheel 150, which is mechanically coupled to the right bracket 330. The motorized front wheel 150 is configured to pivot and control, in part, the direction of the image tracking system 100 in the x-y plane. A passive rear wheel 160 is positioned toward the rear and bottom of the image tracking system 100. Similar to the passive center wheels 145, 255, the passive rear wheel 160 is coupled to the frame 190 through casters, which permit relatively easy pivoting of the passive rear wheel 160 as the image tracking system 100 travels within the x-y plane. While not shown in FIG. 2, the image tracking system 100 further includes a motorized rear wheel 175 (similar to the one shown in FIG. 8), which is mechanically coupled to the rear left of the image tracking system 100. Similar to the motorized front wheel 150, the motorized rear wheel 175 is configured to pivot.

The motorized rear wheel 175, in conjunction with the motorized front wheel 150, controls the direction of the image tracking system 100 in the x-y plane. In other words, the motorized wheels 150, 175 control the forward and backward movement of the image tracking system, in addition to the left and right movement of the image tracking system. In that regard, when a subject 200, who is positioned between the brackets 310, 330 of the image tracking system 100, begins to walk within the x-y plane, the motorized wheels 150, 175 permit the image tracking system 100 to follow the walking subject.

Also, as shown in FIG. 2, the image tracking system 100 also includes power cells 180, which, in some embodiments, are rechargeable. Power cells 180 supply power to the motorized wheels 150, 175 to pivot the wheels 150, 175, as well as drive the wheels 150, 175 forward and backward. Since motorized wheels and their driving mechanisms are known in the art, and one having ordinary skill in the art can construct such a driving mechanism from the description provided above, further discussion of the wheels 150, 175 and their control mechanisms is omitted with reference to FIG. 2. The motorized wheels and their driving mechanisms can be designed for manual operation. Alternatively, the tracking mechanism can be provided with feedback control so that the image tracking system 100 can automatically follow the subject 200, as described in greater detail below.

It should also be appreciated that while six wheels are shown in the embodiment of FIG. 2, the image tracking system 100 can also be constructed with a fewer number or a greater number of wheels. Similarly, while two motorized wheels 150, 175 are explicitly described, it should be appreciated that all of the wheels can be motorized, should one wish to design the image tracking system 100 in that manner. It should also be appreciated that, while power cells 180 are shown in FIG. 2 to provide power to the image tracking system 100, for other embodiments, the image tracking system 100 can be electrically coupled to a power source, such as an outlet, using cables or wires. In that regard, both tethered embodiments (using cables and wires) as well as non-tethered embodiments (using power cells, such as car batteries) are intended to be within the scope of this disclosure.

When the subject 200 begins to walk, not only does the location of the subject 200 in the x-y plane change, but the position of the subject's knee undulates in a time-varying manner. In other words, the movement of the subject's knee is not limited to the x-y plane. Rather, the subject's knee can freely move along the z-axis as the subject 200 travels along the x-y plane, thereby permitting movement of the knee in all three dimensions.

The source 105 and the detector 110 are configured to move in 3D to track the movement of the knee (or other moving anatomy) as the subject 200 walks around. As briefly noted above, once the housings 115, 130 have been coarsely adjusted to their desired height, the vertical and horizontal rails 120, 125, 135, 140 permit the source 105 and the detector 110 to move upward and downward as well as forward and backward. In that regard, the source 105 and detector 110 can move in harmony with the movement of the knee (or other anatomy of interest).

Thus, the wheels 150, 155, 145, 255, 160, 175, which provide movement of the image tracking system 100 along the x-y plane, in combination with the rails 120, 125, 135, 140, which provide movement of the source 105 and the detector 110 along the x-z plane, provide movement of the source 105 and the detector 110 in all three dimensions. The mechanisms for moving the source 105 and the detector 110 within their respective housings 115, 130 can be conventional servo motors, which are known to those having skill in the art. Those mechanisms can be located within the housings 115, 130 or, alternatively, can be located further rearward on the frame 190.

For embodiments in which the mechanisms for moving the source 105 and the detector 110 are located further rearward on the frame 190, various gears, cogs, chains, belts, or other known mechanical coupling mechanisms can be used to convey forces to the source 105 and the detector 110. Those forces then move the source 105 and the detector 110 appropriately along the rails 120, 125, 135, 140. Since various linear servo drive mechanisms, along with corresponding mechanical couplings, are known in the art, and since one having ordinary skill in the art can construct a suitable mechanism for moving the source 105 and the detector 110 in accordance with the above description, further discussion of such mechanisms is omitted with reference to FIG. 2.

Data acquisition and data transfer is next discussed. As shown in FIG. 2, located within the image tracking system 100 are one or more data processing units 165, which also include data acquisition hardware, and one or more data storage units 195. For some embodiments, these data processing units 165 and data storage units 195 can be conventional computer hardware components, such as, for example, a microprocessor-based motherboard, volatile memory, non-volatile memory, etc. The image tracking system further 100 comprises a wireless transceiver 170, which can be used in either tethered embodiments or non-tethered embodiments. The wireless transceiver 170 is configured to transmit data from the image tracking system 100 to an off-site resource for storage and processing. Additionally, the wireless transceiver 170 is configured to receive commands from off-site, which can be relevant to controlling the movement of the image tracking system 100, or to controlling data acquisition parameters associated with the image tracking system 100. Since data processing, data acquisition, data storage, data transmission, and data reception hardware are known in the art, further discussions of these components, in isolation, are omitted with reference to FIG. 2.

Since, in the embodiment of FIG. 2, conventional fluoroscopic components are used in the image tracking system 100, those having ordinary skill in the art will appreciate how images are acquired, stored, and processed. Thus, only a truncated discussion of those aspects is discussed with reference to FIG. 2. In short, the source 105 emits radiation, which passes through a particular anatomical region of the subject 200, and is detected by the detector 110. The detected radiation is used to reconstruct an image of the anatomy that has been irradiated. For some embodiments, conventional fluoroscopic image reconstruction techniques can be employed by the data processing units 165. Hence, no further discussion is provided with reference to image reconstruction techniques.

Various considerations are involved in capturing fluoroscopic images. For example, since fluoroscopy utilizes finite doses of harmful radiation, the radiation dosage is regulated by federal and state governmental standards, which are known to those having skill in the art. Both the radiation dosage for a single image and the aggregate dosage for multiple images over a fixed time period are governed by the appropriate regulatory standards. As is known, the quality of a fluoroscopic image is proportional to the radiation dosage, as well as a host of other factors. For at least that reason, the number of images that can be acquired from a moving subject over a fixed time period (e.g., frames-per-minute (fpm) or frames-per-second (fps)) is limited by the signal-to-noise of the fluoroscopic system, which is affected by the governmentally-allowable radiation dosage.

In addition to the governmental limitations, the data capture is also limited by technological limitations, such as hardware or software limitations. For example, each fluoroscopic image is typically acquired by detecting a finite amount of radiation that has passed through a given anatomy of a subject. That data is captured by, for example, a detector, which converts the detected radiation into a digital signal for processing. The digital signal is indicative of a two-dimensional matrix, which represents the two-dimensional image grid that has been acquired. As is known in the art, the rate at which data can be acquired and digitized is largely a function of the size of the image matrix. For example, higher-spatial-resolution images will have greater hardware demands than lower-spatial-resolution images. Similarly, higher-temporal-resolution images will have greater hardware demands than lower-temporal-resolution images. Specifically, for a finite processor speed and memory capacity, the hardware will limit the number of frames that can be acquired during a fixed time interval, and also the spatial resolution of the images that can be acquired without exceeding the hardware capabilities.

Since one having ordinary skill in the art can readily calculate the maximum data capture rate, given these various factors, further discussion of the data capture rate is omitted here. However, it should be appreciated that a spatial resolution of up to 2K-by-2K pixels, and a temporal resolution of up to 2,000 fps should be sufficient to image a particular anatomical region with both spatial and temporal clarity.

The reconstructed images are then stored on the data storage units 195. Alternatively, the reconstructed images are transferred off of the image tracking system 100 using the wireless transceiver unit 170, thereby permitting off-site processing of the reconstructed images. In fact, as is known in the art, for some embodiments, the raw data from the detector can be transferred off-site (i.e., off of the image tracking system 100) for image reconstruction and processing offsite. Since such data storage and data transfer methods are known in the art, further discussion of data storage and data transfer is omitted here.

However, it should be noted that, for wireless (or non-tethered) embodiments of the image tracking system 100, the data transfer from the image tracking system 100 to an offsite location will be limited by the data transfer rate of the wireless transceiver unit. For example, for some embodiments, the wireless transceiver unit can be an 802.11b-compliant (or 802.11g-compliant) transceiver, which is governed by the Institute of Electrical and Electronics Engineers (IEEE) 802.11b standard. The IEEE standards, and other similar wireless standards, provide the data transfer requirements for all communications systems that are standards-compliant. Since the IEEE standards, and various other wireless standards, are known in the art, only a truncated discussion of such standards is provided here. If the image tracking system 100 is 802.11b-compliant, then the image tracking system 100 cannot transfer data beyond the capacity provided by the 802.11b standard. In that regard, should a greater amount of data be acquired on the image tracking system 100, any excess acquired data will be buffered onboard the image tracking system 100, and transmitted offsite as the data-transfer capacity permits. It should be appreciated that, if less data than the provided bandwidth is acquired, then all of the acquired data can be transmitted offsite without bottle-neck effects that accompany the excess-data-acquisition situation.

In other embodiments, if the collected data exceeds the capacity of the wireless transceiver, then that data can be compressed on the image tracking system 100, in accordance with known compression techniques, thereby effectively improving the data offloading capabilities of the image tracking system 100. For that embodiment, the compressed data, once transmitted to an offsite location, can be uncompressed at the offsite location. In that regard, the wireless bandwidth limitations are somewhat remedied by preprocessing and postprocessing the data.

For yet other embodiments, rather than transmitting all of the data offsite, a sample of the data (e.g., every second frame, every third frame, every tenth frame, etc.) can be transmitted offsite for immediate processing, and the remaining images can be subsequently transmitted offsite when the bandwidth becomes available. By only transmitting samples of the data, much of the bandwidth limitations can be circumvented. However, it should be appreciated that this approach results in a decreased time resolution of the images.

For yet other embodiments, these various techniques can be combined. For example, if the spatial and temporal resolution is extremely fine, as compared to the available bandwidth, then it would be possible to compress a sampling of the data, and transmit the compressed sampled data offsite for immediate processing, and subsequently transfer the remaining data when the bandwidth becomes available. As one can see, once the data transmission capacity (or limitation) is known, various approaches can be taken to accommodate those limitations. Since those approaches will be readily available to those having ordinary skill in the art, further discussion of those approaches is omitted here.

These reconstructed images are used, in conjunction with a feedback mechanism, to track the position of the anatomy that is being imaged. In other words, the resulting images provide the information for suitable 3D movement of the source 105 and the detector 110. The feedback and control of the 3D movement is next discussed.

As noted above, the image tracking system 100 is configured to track a particular anatomical area of a subject 200. In some embodiments, among others, the anatomical region of interest (ROI) is tracked using an image recognition algorithm. For example, a fluoroscopic image of a human knee shows distinct bone areas, which normally appear dark in a fluoroscopic image. Additionally, the knee itself appears brighter than the bones, and also has a distinct shape on the fluoroscopic image. Thus, a subject's knee can be identified on a scout (or initial) image by acquiring an image of the knee and manually labeling the region of interest. Thereafter, for subsequently acquired images, known image recognition algorithms can be used to identify the location of the knee in a particular fluoroscopic image. Since various image recognition algorithms are known in the art, only an abridged discussion of image recognition algorithms is provided here.

As described above, once the knee has been isolated using the image recognition algorithm, the movement of the knee across an image can be tracked by simply finding the relative displacement of the knee within a captured image. For some embodiments, among others, that relative displacement can simply be calculated as a Cartesian offset within a two-dimensional image. For example, if the knee is centered in the originally-acquired scout image, then any deviation of the knee from the center will constitute movement of the knee.

That deviation is used to calculate the appropriate adjustment needed to align the source 105 and the detector 110, so that the image of the knee is substantially centered within the acquired image at all times. For some embodiments, if the knee is determined to be offset forward by one centimeter in an image, then both the source 105 and the detector 110 are moved forward along the horizontal rails 120, 135 by one centimeter, thereby compensating for the relative movement of the knee. Similarly, if the knee is offset in the vertical direction, then corresponding adjustments can be made to the source 105 and detector 110 along the vertical rails 125, 140. Since various mechanical adjustment mechanisms are known in the art, as discussed above, further discussion of the movement of the source 105 and detector 110 is omitted here.

Often, the data limitations stem from data transfer capacity, or bandwidth for data transfer. Rarely will the processor speed or memory be the data limitation. In other words, for data that is acquired and transferred offsite, the limitation on the data arises from the data transfer rate, and not from the data acquisition rate or the data processing rate. Thus, for some embodiments, the image recognition and tracking algorithms are performed onboard the image tracking system 100, thereby reducing any bottlenecking that may arise due to limitations on data capacity. However, it should be appreciated that, for other embodiments, the image recognition and tracking algorithms can also be processed in a remote location that is offsite of the image tracking system 100.

Figure 3:
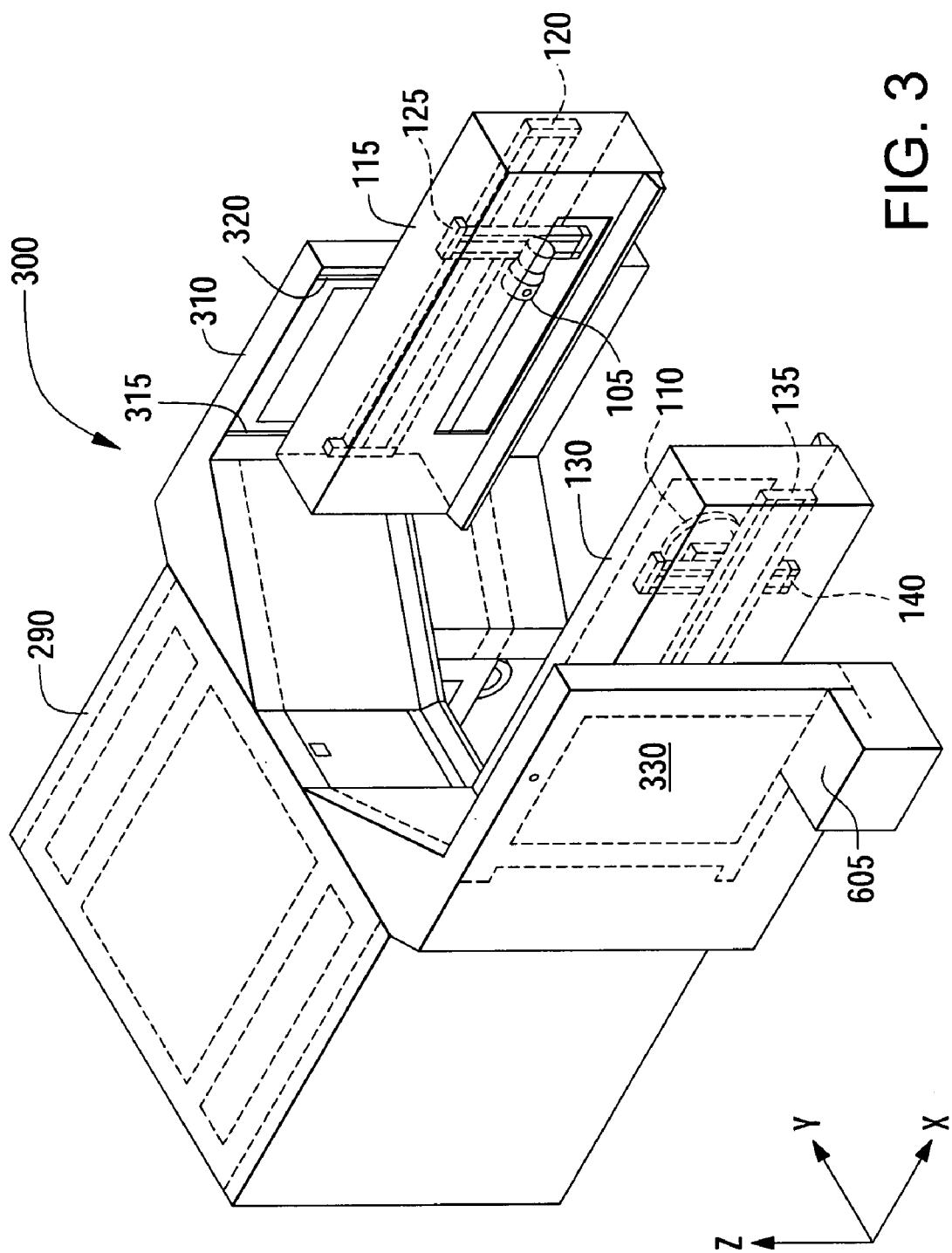
FIG. 3 is a right perspective view of another embodiment of an image tracking system, in which the image tracking system has been set to image a subject's knees.

FIG. 3 is a right perspective view of another embodiment of an image tracking system 100, in which the image tracking system has been set to image a subject's knees. Unlike the embodiment of FIGS. 1 and 2, the image tracking system 300 of FIG. 3 has a different frame 290, which accommodates the various components shown in FIG. 2. Similar to FIGS. 1 and 2, the image tracking system 300 of FIG. 3 includes a left bracket 310 and a right bracket 330, between which a subject can be positioned.

The left bracket 310 accommodates the source housing 115, which houses the source 105. The right bracket 330 accommodates the detector housing 130, which houses the detector 110. The source 105 and the detector 110 are positioned on vertical rails 125, 140, which permit movement of the source 105 and detector 110 in the z-direction. Additionally, the source 105 and the detector 110 are positioned on horizontal rails 120, 135, which permit movement of the source 105 and the detector 110 in the x-direction. The source housing 115 and the detector housing 130 are positioned on housing rails 315, 320, 350, 355, which permit coarse adjustment of the height of the housings 115, 130 in the z-direction.

In addition to these components, the embodiment of FIG. 3 has a wheel cover 605, which prevents, to a certain degree, foreign objects from interfering with the motion of the wheel 150.

As shown in FIG. 3, the image tracking system 300 is configured to image a subject's knee. In that regard, the source housing 115 and the detector housing 130 have been coarsely adjusted and raised to the approximate position of a subject's knees. Thus, when the subject begins to walk or move, the source 105 and the detector 110 can track the position of the subject's knee, once the initial location of the knee has been discerned from the scout image, as described above. It should be appreciated that, during normal walking, the knee likely experiences both vertical (z-direction) motion and horizontal (x-direction) motion. Thus, both vertical and horizontal movement of the source 105 and the detector 110 are expected. In order to minimize the mechanical strains that accompany such movement, the housings 115, 130 are designed to be sufficiently large, for some embodiments, so that the source 105 and the detector 110 can move within their respective housings 115, 130, without having to move the housings 115, 130 as the knee moves.

Figure 4:
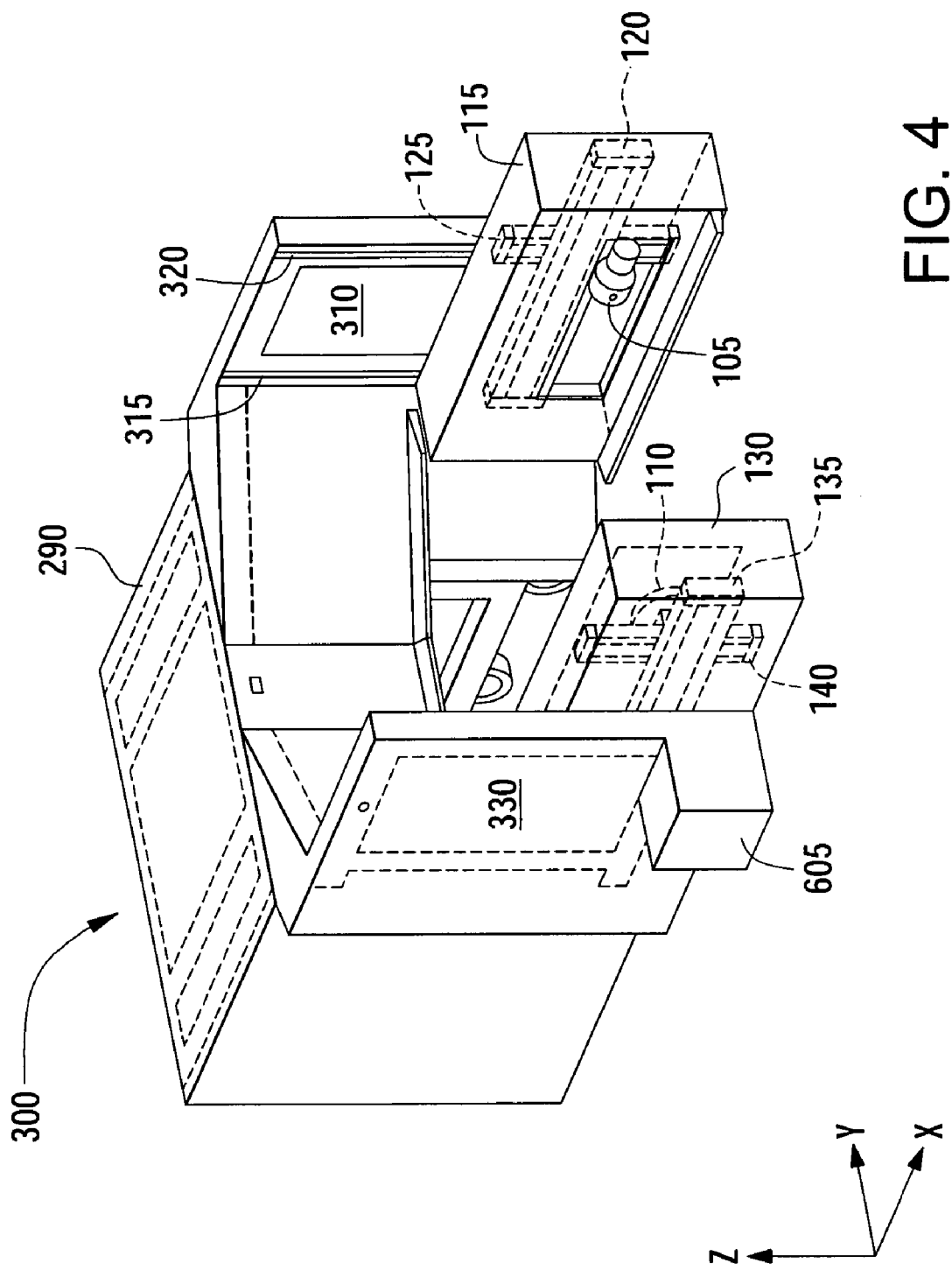
FIG. 4 is a right perspective view of the image tracking system of FIG. 3, in which the image tracking system has been set to image a subject's ankles.
Figure 5:
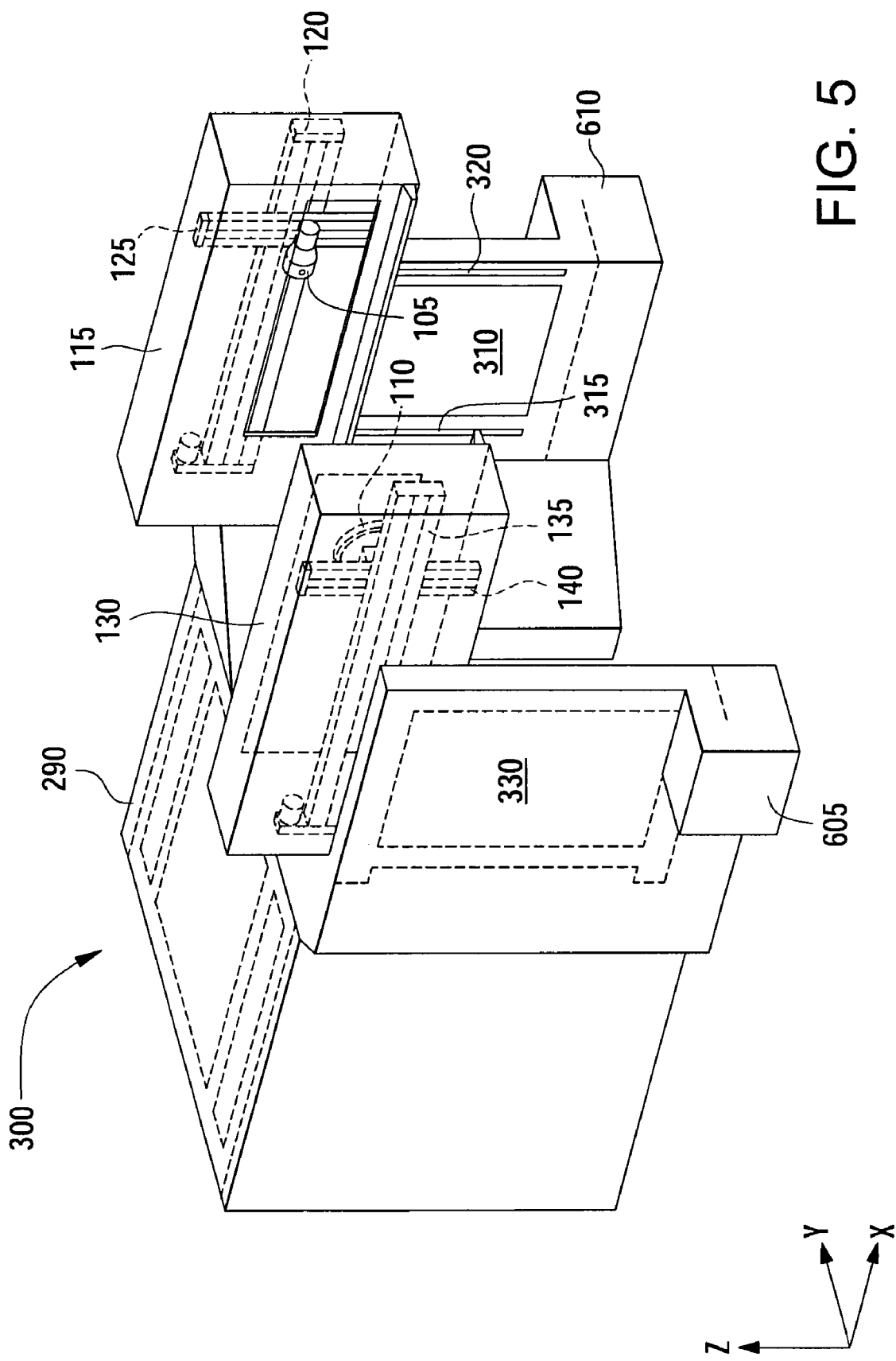
FIG. 5 is a right perspective view of the image tracking system of FIG. 3, in which the image tracking system has been set to image a subject's hips.

FIG. 4 is a right perspective view of the image tracking system 300 of FIG. 3, in which the image tracking system 300 has been set to image a subject's ankles. As shown in FIG. 5, the source housing 115 and the detector housing 130 have been coarsely adjusted and lowered to the approximate position of a subject's ankles. In that regard, when the subject begins walking or moving, the source 105 and the detector 110 can track the position of the subject's ankle. It should be appreciated that imaging of the ankle likely results in greater movement of the source 105 and the detector 110 in the x-direction than in the z-direction. In some studies, the acceleration accompanying the movement of the ankles has been measured to be as high as two (2) g's.

FIG. 5 is a right perspective view of the image tracking system 300 of FIG. 3, in which the image tracking system 300 has been set to image a subject's hips. As shown in FIG. 5, the source housing 115 and the detector housing 130 have been coarsely adjusted and raised to the approximate position of a subject's hips. In that regard, when the subject begins walking or moving, the source 105 and the detector 110 can track the position of the subject's knees. The imaging of the hips is somewhat different from the imaging of either the knees or the ankles. For example, while the subject's anterior-posterior axis is aligned to the x-axis for imaging of knees and ankles, the subject's anterior-posterior axis is aligned to the y-axis for imaging of the hips. The reason being that, normally, it is desirable to obtain a frontal image for hip imaging.

In that regard, rather than traveling along in the x-direction, the image tracking system 300, for hip imaging, will likely travel in the y-direction as the subject walks or moves. Since, as noted above, the wheels are mounted on casters that permit pivoting of the wheels, the image tracking system 300 can easily travel in any direction within the x-y plane.

It should be appreciated that, while imaging of ankles, knees, and hips have been explicitly described above, the image tracking system 300 can also be configured to track the movement of shoulders, arms, and spine, for example, during a golf swing. For those portions of the anatomy, the size, location, and movement of the housings 115, 130, as well as the range of motion of the source 105 and the detector 110 can be altered to accommodate the range of motion of the shoulders, arms, and spine.

In an exemplary embodiment, image tracking systems for upper-body imaging can be configured substantially as a robotic arm, on which the various imaging components are located. While specifically described as a robotic arm, it should be appreciated that the imaging system can be mounted on any type of articulated mechanism that permits full rotational motion.

Also, it should be appreciated that the image tracking system 300 can be readily modified to track movement of subjects on an operating table. For example, when a subject is supine on a surgery table, and real-time imaging of a surgical procedure is desired, a modified image tracking system can be configured to track a particular anatomy of the subject, in the event that the subject is moved while on the operating table.

For those embodiments, the tuning-fork-like arms can be rotated so that one arm is located vertically with reference to the other arm. In other words, the image tracking system 300 can be rotated so that the source-detector axis is along the z-axis, rather than along the y-axis as shown in the drawings. Once the arms are appropriately positioned, the patient can then be positioned between the arms.

For minimally invasive surgery on joints, such as, for example, knees and hips, this type of configuration provides a "Hands-Free" or a "Fully Automated" fluoroscopy unit. Unlike conventional units, in which a surgeon or one of the surgery staff manually manipulates the fluoroscopy unit as the joint moves, and the images are taking out of different planes due to movement, this new configuration permits imaging within substantially the same plane. For example, a surgeon can turn the unit on using, for example, a foot pedal or verbal control. Thereafter, the unit can realign itself with the joint under operation, in substantially the same plane as that prior to movement of the joint.

For such surgical navigation fluoroscopy, each time the surgeon desires a stream of images (video), the unit can be turned on, and the joint of interest will always remain in substantially the same plane, thereby giving the surgeon the optimal view of the desired part of the body.

During minimally invasive surgery the entry is now approximately five inches or less. Due to the size of the incision, the surgeon sees less of the knee than with larger incisions. With the above-described motion-tracking unit, the surgeon will be able to see the joint (e.g., knee, ankle, elbow, or any other part of body) in the same plane allowing for better referencing during surgery.

Figure 6:
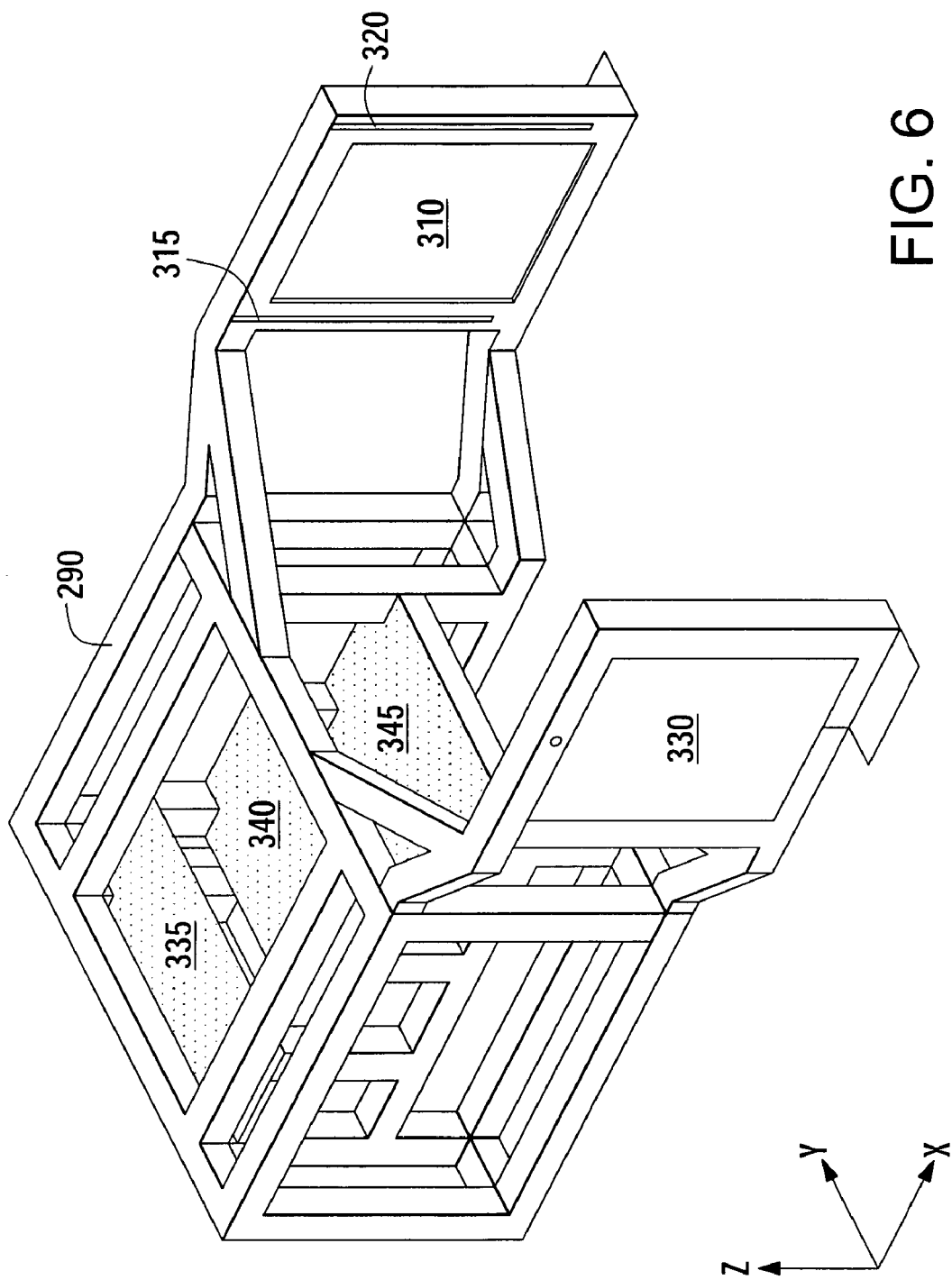
FIG. 6 is a right perspective view showing the frame of the image tracking system of FIG. 3.

FIG. 6 is a right perspective view showing the frame 290 of the image tracking system of FIG. 3. As shown in FIG. 6, in some embodiments, the frame comprises tubular components, which provide structural integrity to the image tracking system 300. The rear of the frame comprises various platforms 335, 340, 345, which accommodate the power sources and processing components, as described above. While a particular embodiment is shown in FIG. 6, it should be appreciated that the frame may be configured to different geometric shapes and sizes in order to accommodate various hardware and mechanical needs.

Figure 7:
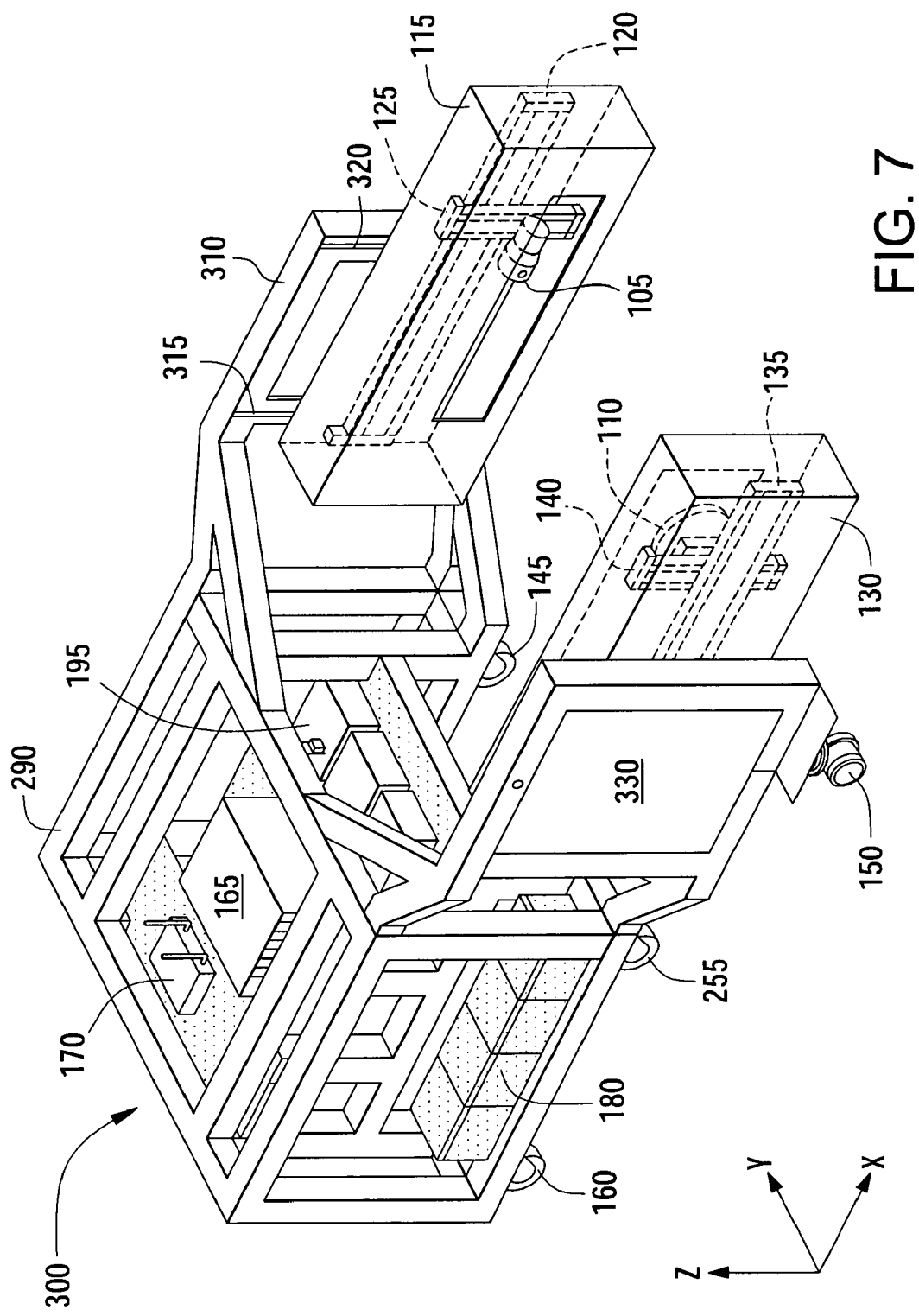
FIG. 7 is a right perspective view showing internal components associated with the image tracking system of FIG. 3.
Figure 8:
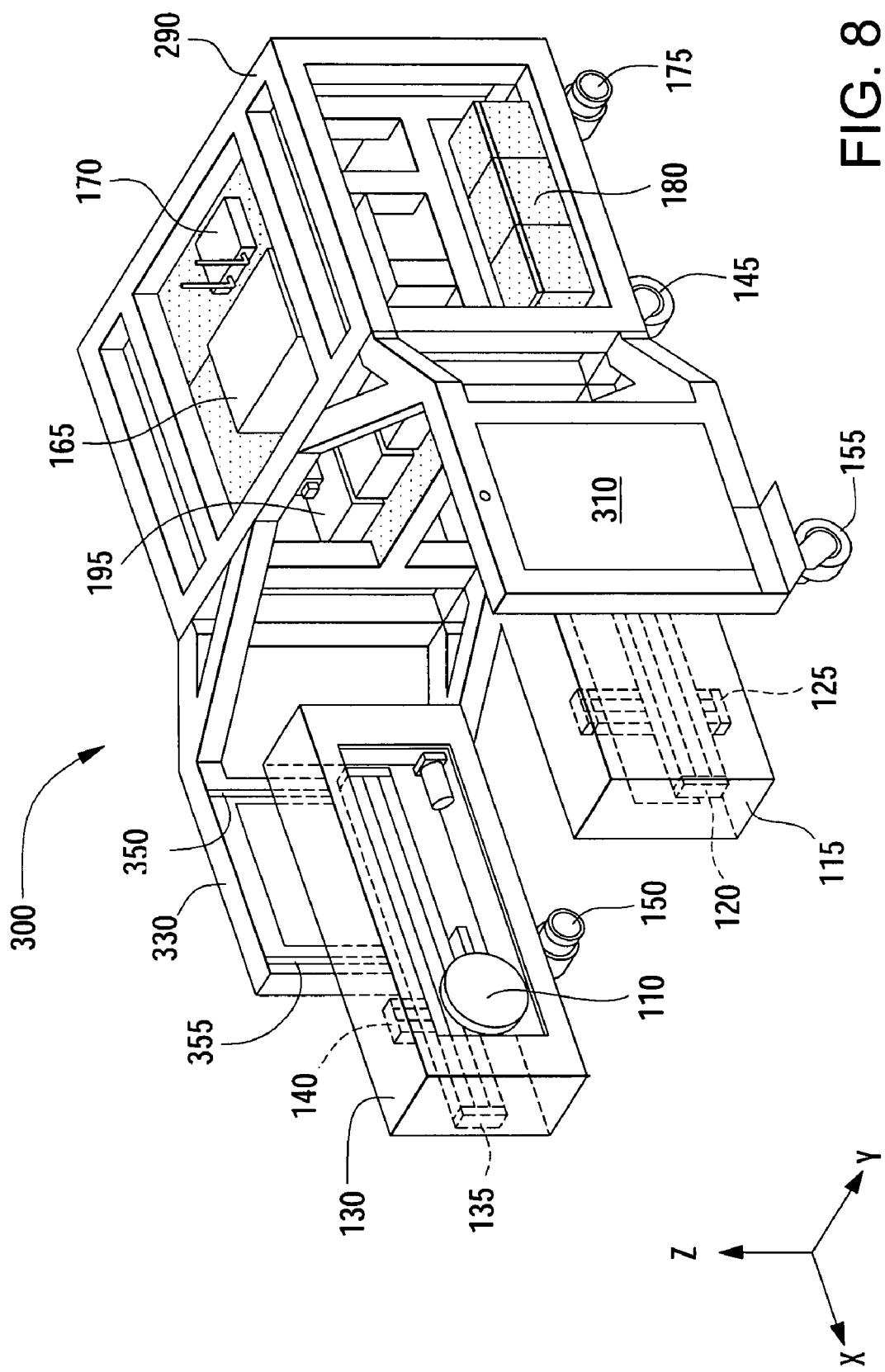
FIG. 8 is a left perspective view showing internal components associated with the image tracking system of FIG. 3.

FIG. 7 is a right perspective view showing the internal components associated with the image tracking system 300, while FIG. 8 is a left perspective view showing the internal components associated with the image tracking system 300. Since these components have been described in great detail with reference to the preceding figures, further discussion of these components is omitted with reference to FIG. 7.

Figure 9:
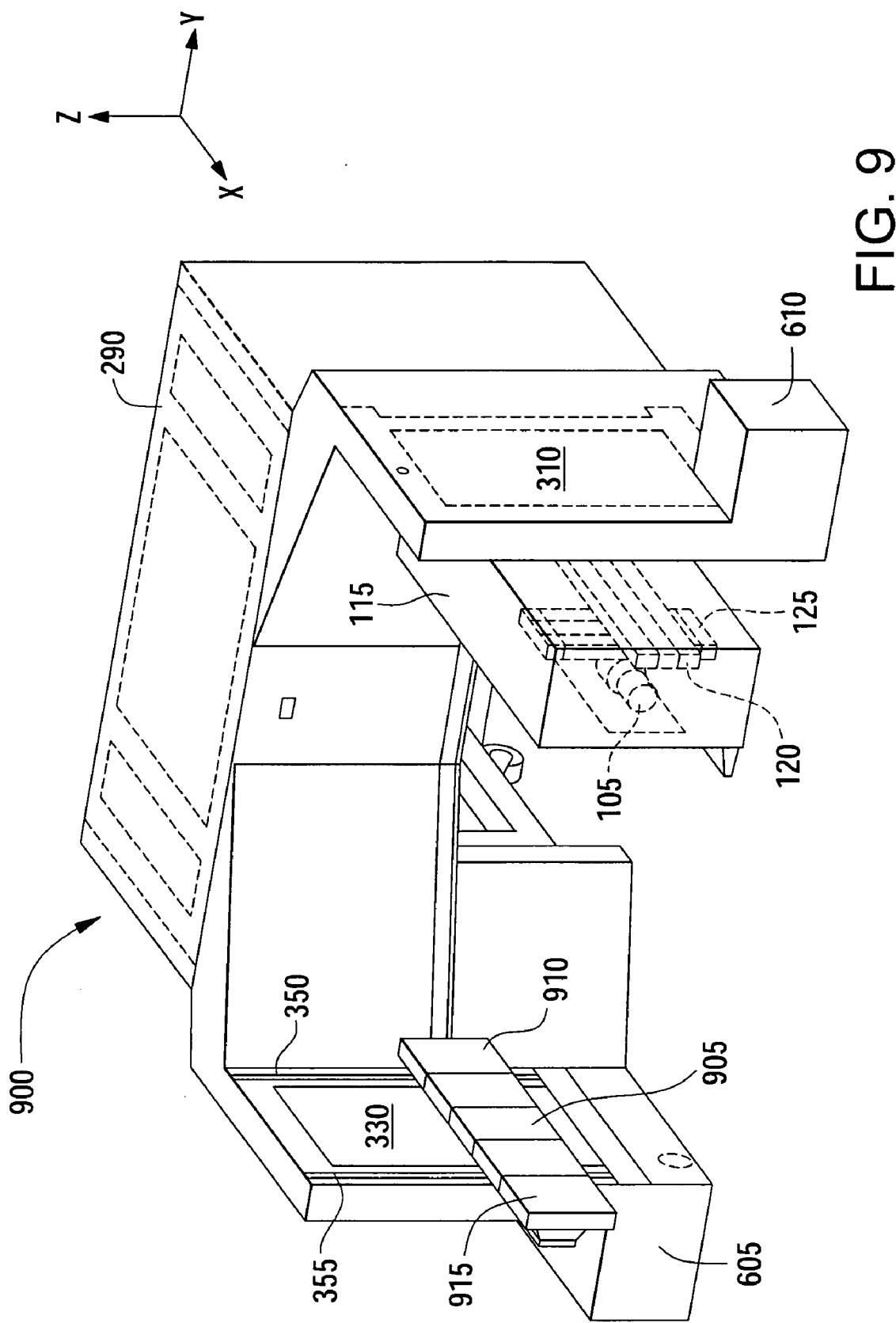
FIG. 9 is a left perspective view of another embodiment of an image tracking system, which employs solid state detector arrays for detection.

FIG. 9 is a left perspective view of another embodiment of an image tracking system 900, which employs solid state detector arrays 905 for detection. Unlike the embodiments of FIGS. 1 and 3, which employ a movable detector 110 that is mounted on rails 135, 140, the embodiment of FIG. 9 employs a solid state detector array 905, which need not move in synchronicity with the source 105.

In operation, when the source 105 moves backward (negative x-direction), the rear portions 910 of the array 905 will detect the radiation that is emitted from the source 105. Conversely, as when the source 105 moves forward (positive x-direction), the front portion 905 of the array 905 will detect the radiation that is emitted from the source 105. For simplicity, the portion of the detector, which detects the emitted radiation, is referred to herein as the "activated" portion of the detector 905. As is known in the art, the detected radiation from the "activated" portion of the array 905 emulates the behavior of the moving detector 110 from the other embodiments of the image tracking system 100, 300. However, unlike those embodiments, the solid state detector array 905 reduces power consumption by eliminating the motors (and other mechanisms) associated with the dynamic movement of the detector 110.

While not shown in FIG. 9, it is also possible to reduce power consumption by mounting the source 105 onto a pivoting joint, such as, for example, a ball joint (not shown). In that regard, rather than providing a translating motion (Cartesian coordinate system with movement along the x-direction and z-direction) for the source 105, a rotating motion (spherical coordinate system with pivoting movement along two orthogonal angular reference frames) can be imparted to the source 105. Stated differently, the source 105 can be configured to alter the directionality of the x-ray emission source, rather than the location of the x-ray emission source. Thereafter, the solid-state detector array 910 can detect the emitted radiation from the source 105.

The reduction of translational moving parts results in reduced energy consumption by the image tracking system 900. Additionally, as can be appreciated by those having skill in the art, both the pivoting configuration and the translating configuration provides for a moving field of view, which corresponds to the location of the anatomical region of interest.

Figure 10:
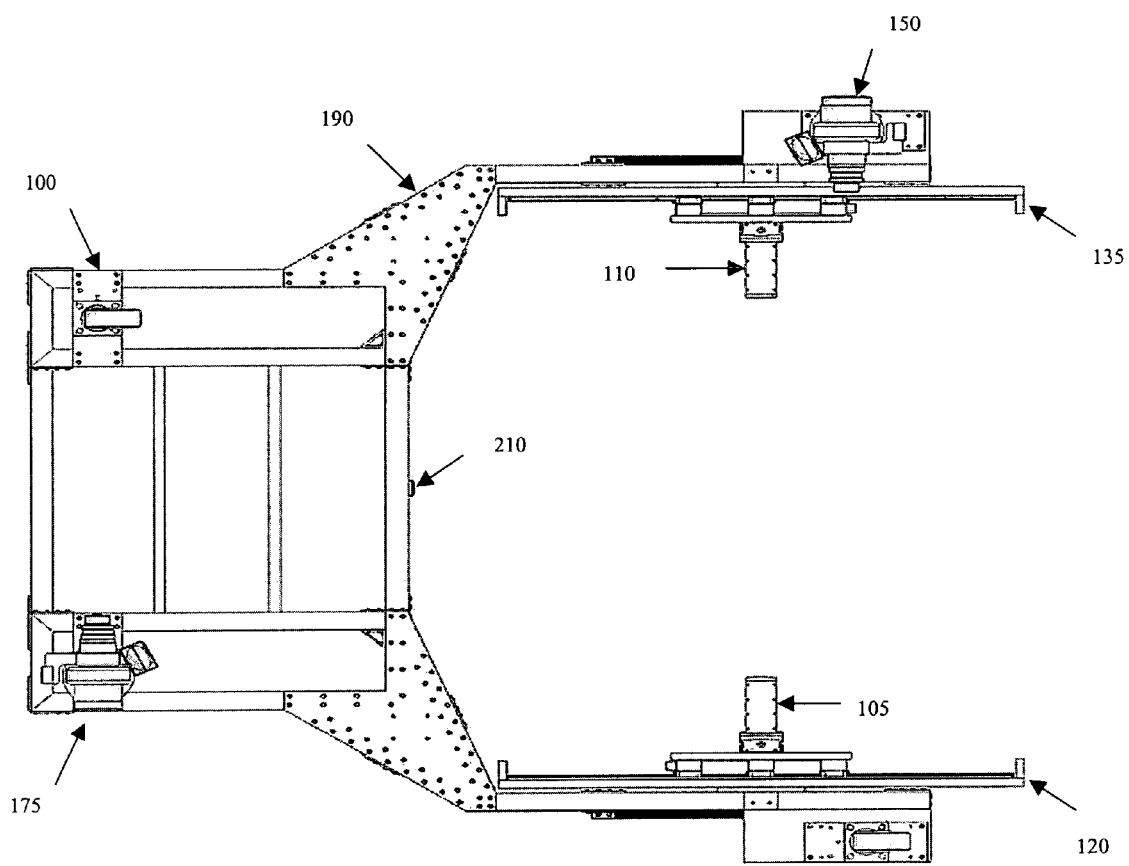
FIG. 10 is a bottom view of the image tracking system of FIG. 1 including a subject tracking system.

As mentioned above, in one embodiment the subject is placed on a treadmill positioned in the imaging cavity between horizontal rails 120 and 135. The movement of, for example, a knee, ankle or hip is tracked and fluoroscopic images of the particular joint captured. In another embodiment, a subject tracking system can be incorporated into the image tracking system. In this embodiment, a treadmill is not used. Instead, the subject is allowed to walk freely about the room. The subject tracking system allows the image tracking system to follow the subject as the subject walks about the room. An exemplary subject tracking system is a laser tracking system including tracking laser 210, as illustrated in FIG. 10. Tracking laser 210 is coupled to controls that automatically drive the motorized independent front and rear wheels 150, 175 to maintain the subject positioned within the imaging cavity between imaging source 105 and detector 110. Ideally, the subject tracking system maintains the image tracking system 100 positioned about the subject so that images of the subject's knee or ankle are taken while the subject is walking towards tracking laser 210 in a path parallel to horizontal rails 120 and 135. In the case where images are to be taken of a hip, ideally, the subject tracking system maintains image tracking system positioned about the subject so that images are taken while the subject is walking towards either imaging source 105 or detector 110.

The image tracking system of the present disclosure can also include safety monitoring systems and controls to protect the subject and the equipment. Any one of these systems can be used alone, or alternatively two or more of the systems can be used to provide multi-layer independent systems.

Figure 11:
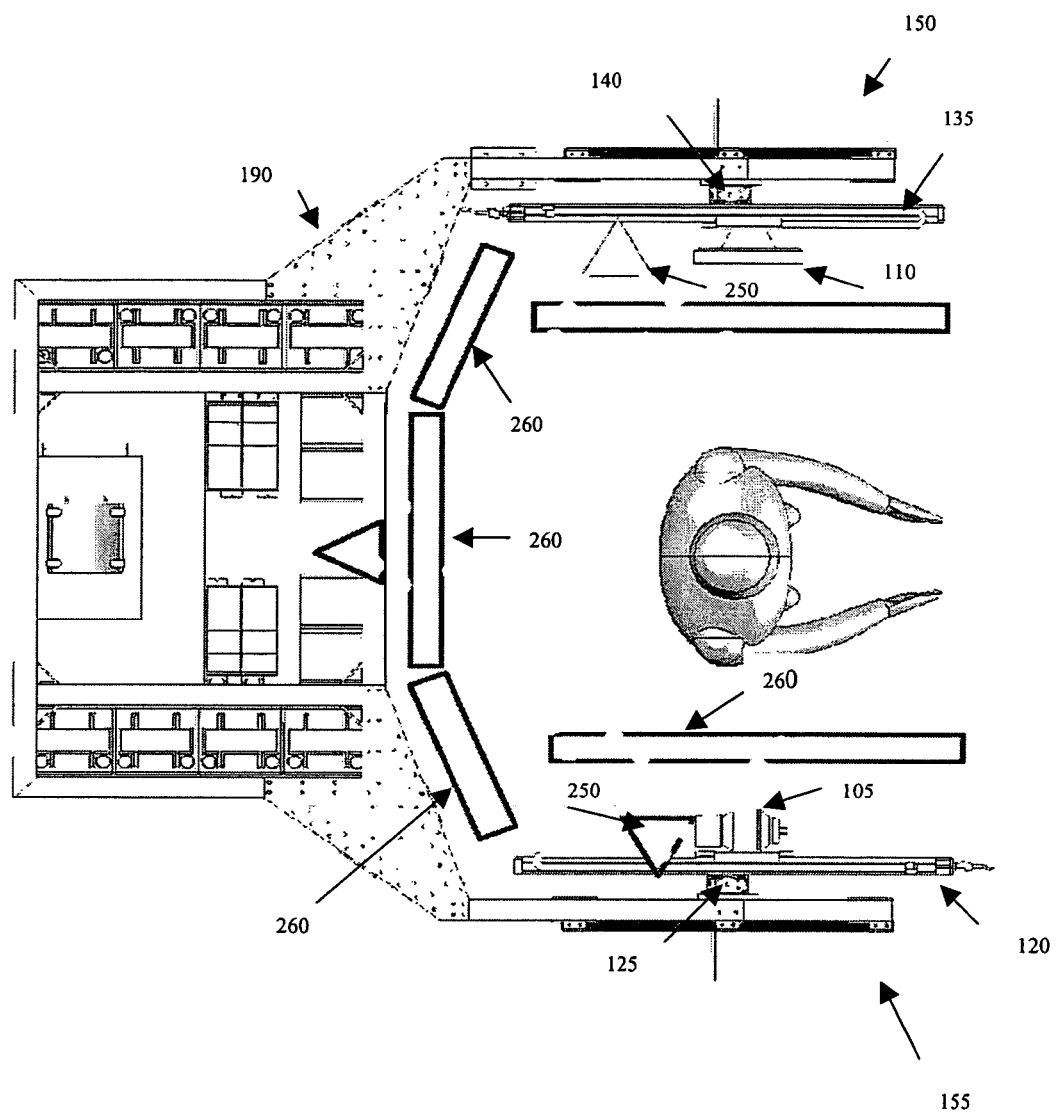
FIG. 11 is a top view of the image tracking system of FIG. 1 including subject standoff sensors.

One available system in sustaining safe subject tracking control is to monitor the magnitude of the standoff distance between the subject and various points on the frame within the measurement cavity, as illustrated for example in FIG. 11. This can be done with independent sensors 250 and processing electronics that provide fast response and that are independent of the main on-board computers. Another system of defense can be contact or proximity sensors 260 (e.g., bumper switches or light curtains) integrated into the imaging cavity that would pickup the occurrence of physical contact between the subject and the frame and would shutdown the entire system immediately. Yet another system of defense can be to monitor the operational levels and conditions of the frame drive motors. Motor currents reflect load conditions and can be compared with speed values to determine if the chassis has encountered an obstruction (e.g., running into a fallen subject). Drive wheel accelerations and speeds can also be monitored continuously to determine if they are within appropriate bounds.

Figure 12:
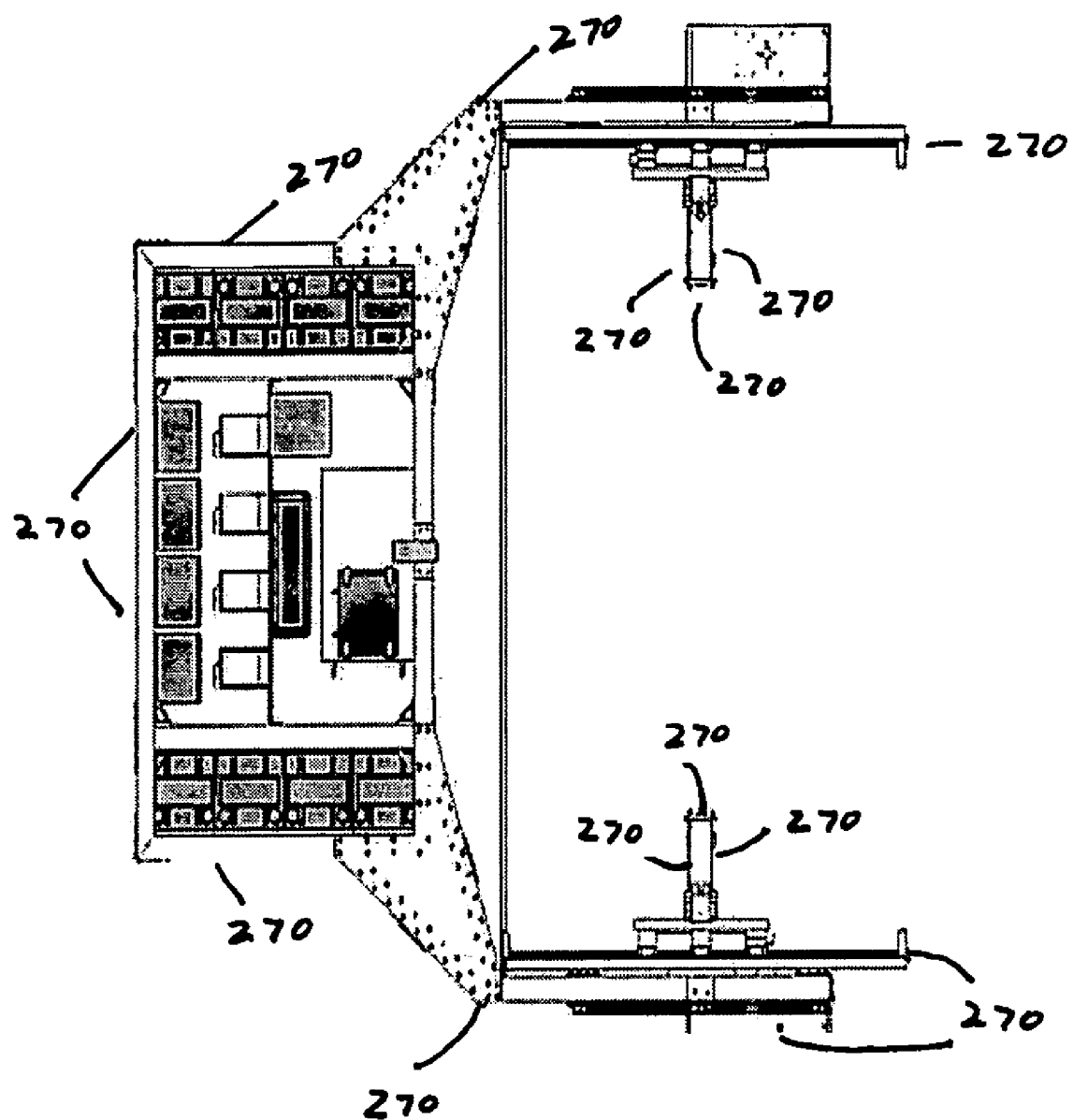
FIG. 12 is a top view of the image tracking system of FIG. 1 including sensors for external protection of the system.

The drive currents to the frame drive motors can be limited to specific values that constrain accelerations consistent with procedures being performed. Multiple E-stops including remote control push-button, "dead man" pull cords, and hard-wired radio E-stops can be implemented for additional layers of safety. Separate safety control channels can be provided to protect the image tracking system from colliding with fixed objects and equipment that might be present. Sonar sensors 270 surrounding the perimeter of the frame as shown in FIG. 12 can provide an active barrier as has been done in numerous mobile robotics systems. If the image tracking system moves within, for example, one meter of an external object, power to all drives would be zeroed and the drive motor brakes applied. Considering the maximum speed capability (~2.2 m/sec) and mass of the image tracking system (~400 kg), a one meter buffer zone would be sufficient to halt the machine well before any contact.

As shown from the various embodiments of the image tracking system 100, 300, 900, various anatomical regions of a subject can now be imaged as the subject is moving. Thus, unlike conventional fluoroscopic imaging systems, which are relatively sedentary, the image tracking systems 100, 300, 900 permit dynamic acquisition of images from dynamically moving anatomical regions. The dynamically acquired data provides a more realistic view of, for example, joints as the joints engage in normal physiological movements.

The data acquisition techniques, the data processing techniques, and the data transfer techniques may be implemented in hardware, software, firmware, or a combination thereof. In the preferred embodiment(s), these techniques are implemented in software or firmware that is stored in a memory and that is executed by a suitable instruction execution system. If implemented in hardware, as in an alternative embodiment, these techniques can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Given the system diagrams of FIGS. 1 through 12, one having ordinary skill in the art should readily appreciate various methods that correspond to the above-described systems.

Although exemplary embodiments have been shown and described, it will be clear to those of ordinary skill in the art that a number of changes, modifications, or alterations to the invention as described may be made. For example, while various embodiments have been shown, in which the image tracking system 100, 300, 900 tracks the movement of a roaming subject, it should be appreciated that the subject can be placed on a treadmill or other similar device, and various movements of the joints can be tracked and imaged as the subject walks or moves on the treadmill. For that embodiment, power is conserved for the image tracking system 100, 300, 900, since less power is used to provide mobility for the entire image tracking system 100, 300, 900.

Also, while various embodiments have been disclosed in which conventional techniques can be used, it should be appreciated that those conventional techniques can be modified or customized in accordance with the various needs of a particular environment or operator. For example, while conventional data acquisition techniques for fluoroscopy have been disclosed, it should be appreciated that customized data acquisition techniques can also be employed with the image tracking systems 100, 300, 900. Likewise, while conventional data storage approaches are disclosed for convenience, it should be appreciated that the data can be stored in a proprietary or conventional format. Additionally, while conventional fluoroscopic data processing techniques are disclosed to better teach various aspects of the invention, it should be appreciated that the data processing techniques can be modified in a variety of ways without detriment to the scope of the disclosure. Also, while conventional image recognition programs and conventional image tracking algorithms have been described in conjunction with the image tracking system's control mechanism, it should be appreciated that the image recognition programs and the image tracking algorithms may be customized algorithms that better accommodate the recognition and tracking of, for example, the human anatomy.

All such changes, modifications, and alterations should therefore be seen as within the scope of the disclosure.

What is claimed is:

1. An image tracking system, comprising:
a first bracket;
a second bracket;
a source mounted to the first bracket;
a detector mounted to the second bracket, the source and the detector, in combination, being configured to define a field-of-view, wherein the first bracket and the second bracket are reconfigurable in at least two axes of movement to reposition the detector and the source;
the source and the detector utilized to obtain an image of an anatomical region of interest located within the defined field-of-view; and
a motor-driven portable ground carriage that includes carriage control circuitry configured to automatically control repositioning of the ground carriage responsive to movement of the anatomical region of interest;
wherein the first bracket and the second bracket are mounted to the portable ground carriage.

2. The system of claim 1, further comprising:
image processing logic configured to process the image; and
image identification logic configured to identify a predefined anatomical feature within the anatomical region of interest.

3. The system of claim 2, further comprising:
image tracking circuitry configured to track movement associated with the predefined anatomical feature; and
bracket control circuitry configured to control reconfiguring of the first bracket and movement of the source, the movement of the source being correlated to the movement of the predefined anatomical feature within the defined field-of-view.

4. The system of claim 1, wherein the source is pivotally mounted to the first bracket.

5. The system of claim 1, wherein the source is translationally mounted to the first bracket.

6. The system of claim 1, wherein the detector comprises a solid-state detector array.

7. The system of claim 1, wherein the detector comprises an imageintensifier.

8. The system of claim 1, wherein the detector is translationally mounted to the second bracket.

9. The system of claim 1, wherein:
the first bracket is reconfigurable to allow vertical and horizontal movement of the source;
the second bracket is reconfigurable to allow vertical and horizontal movement of the detector; and,
the source and the detector are configured to move substantially synchronously with each other.

10. The system of claim 1, further comprising:
a source motor operatively coupled to the source, the source motor is configured to control the movement of the source; and
a detector motor operatively coupled to the detector, the detector motor is configured to control the movement of the detector; and
wherein the source motor and the detector motor are configured to move substantially synchronously with each other.

11. An image tracking system, comprising:
a first bracket including a first guide and a second guide, where the first guide includes a range of motion non-parallel to a range of motion of the second guide;
a second bracket including a third guide and a fourth guide, where the third guide includes a range of motion non-parallel to a range of motion of the fourth guide;
a source mounted to at least one of the guides of the first bracket, the first guide and the second guide cooperating with each other to allow at least two-dimensional translational motion of the source;
a detector mounted to at least of the guides or the second bracket, the third guide and the fourth guide cooperating with each other to allow at least two-dimensional translational motion of the detector;
a field-of-view position controller for controlling movement of the source and the detector responsive to dynamic motion of an anatomical region of interest.

12. The system of claim 11, further comprising:
a motor-driven portable ground carriage that includes carriage control circuitry configured to automatically control repositioning of the ground carriage responsive to movement of the anatomical region of interest;
wherein the first bracket and the second bracket are mounted to the portable ground carriage.

13. The system of claim 11, wherein the source includes an x-ray fluoroscopic source.

14. The system of claim 9, wherein the detector includes an x-ray fluoroscopic source.

15. The system of claim 11, wherein the first guide includes a vertical rail.

16. The system of claim 11, wherein the second guide includes a horizontal rail.

17. The system of claim 11, wherein the third guide includes a vertical rail.

18. The system of claim 11, wherein the fourth guide includes a horizontal rail.

19. The system of claim 11, wherein the two-dimensional translational motion comprises:
motion in at least two axes of a three-dimensional coordinate system including vertical motion in a Y-axis, lateral motion in a X-axis, and depthwise motion in a Z-axis.

20. An imaging system, comprising:
a first bracket;
a second bracket;
a source mounted to the first bracket, the source configured to travel vertically along the first bracket, the source further configured to travel horizontally along the first bracket;
a detector mounted to the second bracket, the detector configured to travel vertically along the second bracket, the detector further configured to travel horizontally along the second bracket, the source and the detector configured to move substantially synchronously with each other;
an image acquisition circuit for dynamically acquiring images over time;
an image identifying circuit for identifying a region of interest within the acquired images;
an image tracking controller for tracking the region of interest over time;
a source controller for controlling the movement of the source, the source controller configured to move the source as a function of the tracked region of interest over time; and
a detector controller for controlling the movement of the detector, the detector controller configured to move the detector as a function of movement of the tracked region of interest over time.

21. An image tracking system, comprising:
a source configured to emit radiation;
a detector located opposite the source to include a field of view therebetween, the detector configured to detect emitted radiation from the source;
image circuitry operatively coupled to the detector, the image circuitry using outputs from the detector to generate images of an anatomical region of interest responsive to the anatomical region of interest dynamically occupying at least a portion of the field-of-view; and
control circuitry operative to automatically control repositioning of the detector and the source to substantially preserve the anatomical region of interest within the field-of-view as the anatomical region of interest is repositioned under load within the field-of-view.

22. A method of generating images of an anatomical region of interest, the method comprising:
configuring a radiation source and a radiation detector to establish a field of view between the radiation source and the radiation detector for an anatomical region of interest;
repositioning at least one of the radiation source and the radiation detector to maintain the anatomical region of interest within the field of view while the anatomical region of interest is moving through at least a portion of its range of motion under loaded conditions;

emitting radiation from the radiation source at least substantially simultaneously with the act of repositioning at least one of the radiation source and the radiation detector;

detecting at least a portion of the radiation emitted from the radiation source as the anatomical region of interest is moved through at least a portion of its range of motion under loaded conditions;

generating detection data in response to the act of detecting the radiation emitted from the radiation source while the anatomical region of interest is moved through at least a portion of its range of motion under loaded conditions; and dynamically generating images of the anatomical region of interest based upon the detection data generated.

23. A method of initializing an image tracking system, the method comprising:

acquiring an initial image of an anatomical feature;

manipulating the initial image to generate identification data that identifies an anatomical region of interest;

processing the identification data to establish processed identification data for use by an image recognition algorithm; and initializing a controller operative to reposition at least one of a radiation source and a radiation detector, based upon the processed identification data and a changing position of the anatomical feature during loaded dynamic movement of the anatomical feature, where the controller includes the image recognition algorithm.

24. The system of claim 2, further comprising:

image tracking logic configured to track movement associated with the predefined anatomical feature; and control circuitry configured to control reconfiguring of the second bracket and movement of the detector, where movement of the detector is correlated to movement of the predefined anatomical feature.

25. The system of claim 12, further comprising a combination controller including the field-of-view position controller and the carriage control circuitry.

26. A method of generating images of an anatomical region of interest, the method comprising:

configuring a radiation source and a radiation detector to establish a field of view therebetween for an anatomical region of interest;

emitting radiation from the radiation source while the anatomical feature of interest is dynamically repositioned under load within the field of view;

detecting at least a portion of the radiation emitted from the radiation source while the anatomical feature of interest is dynamically repositioned under load within the field of view, where the detected emitted radiation comprises detection data;

repositioning the radiation source and the radiation detector to maintain the anatomical region of interest within the field of view while the anatomical region of interest is dynamically repositioned under load; and generating images of the anatomical region of interest using the detection data.

* * * * *